United States Patent [19]

Tachibana et al.

[11] Patent Number: 5,254,534
[45] Date of Patent: Oct. 19, 1993

[54] ADJUVANT FOR CANCER IMMUNOTHERAPY

[75] Inventors: Masaaki Tachibana; Hiroshi Tazaki, both of Tokyo, Japan

[73] Assignees: Green Cross Corporation, Osaka; Milk Industry Co., Tokyo, both of Japan

[21] Appl. No.: 303,219

[22] Filed: Jan. 30, 1989

[30] Foreign Application Priority Data

Jan. 29, 1988 [JP] Japan .................................. 63-17423

[51] Int. Cl.$^5$ .............................................. A61K 37/02
[52] U.S. Cl. ..................................... 514/12; 424/85.1; 530/350; 530/351
[58] Field of Search ............... 424/85.1; 530/350, 351; 514/12

[56] References Cited

U.S. PATENT DOCUMENTS

| | | | |
|---|---|---|---|
| 4,789,658 | 12/1988 | Yoshimoto et al. | 514/12 |
| 4,847,325 | 7/1989 | Shadle et al. | 514/12 |
| 4,863,902 | 9/1989 | Amagase et al. | 514/12 |
| 4,963,354 | 10/1990 | Shepard et al. | 514/12 |
| 5,104,650 | 4/1992 | Ralph et al. | 424/85.1 |

OTHER PUBLICATIONS

Ladner, M. et al., *The EMBO Journal*, 6 (9): 2693-2698, 1987.
Kawasaki, E., et al., *Science*, 230: 291-296, Oct. 1985.
Ralph, P., et al., *Cellular Immunology*, 76: 10-21 (1983).

*Primary Examiner*—Lester L. Lee
*Attorney, Agent, or Firm*—Sughrue, Mion, Zinn, Macpeak & Seas

[57] ABSTRACT

An adjuvant for cancer immunotherapy with an immuno-activating agent, which comprises a colony stimulating factor as an active ingredient, can remarkably increase the antitumor effect of said immunoactivating agent.

6 Claims, No Drawings

ADJUVANT FOR CANCER IMMUNOTHERAPY

FIELD OF THE INVENTION

This invention relates to an adjuvant comprising a colony stimulating factor as active ingredient and intended for use in cancer immunotherapy with an immunoactivating agent. More particularly, the invention relates to an adjuvant for cancer immunotherapy which, when used in combination with an immunoactivating agent, can increase the efficacy of said immunoactivating agent.

BACKGROUND OF THE INVENTION

Colony stimulating factors (hereinafter referred to as "CSFs") are endogenous factors promoting the proliferation and differentiation of granulocytes and macrophages. The CSFs act on stem cells of the bone marrow granulocytic and macrophage series (GM-CFUs) and are classified, for example, into 1) G-CSF (granulocyte CSF) causing formation of granulocytes, 2) M-CSF (macrophage CSF) causing formation of monocytic macrophages, and 3) GM-CSF causing formation of both granulocytes and macrophages. CSF which belongs to M-CSF and does not act directly on the GM-CFUs but acts on monocytes in the blood to thereby promote secretion of GM-CSF and indirectly cause proliferation of macrophages and granulocytes, has also been purified from human urine (hereinafter referred to as "CSF-HU").

The immunoactivating agent has been used as a means of cancer immunotherapy and, specific examples thereof include Picibanil (OK-432), Krestin (PSK), lentinan and schizophyllan. Picibanil is a polysaccharide in the form of dry powder prepared by lyophilizing the strain of *Streptococcus piogenes* A-III-Su previously treated with penicillin (manufactured by Chugai). Krestin is hot water extract of mycelium of *Criolus versicolor,* which containing mainly a-protein-binding polysaccharide (manufactured by Kureha-Sankyo). Lentinan is a β-1,3-glucan extracted from fruit body of *Leutinus ebodes* (manufactured by Ajinomoto-Morishita-Yamanouchi). Schizophyllan is a polysaccharide, containing β-1,3-glucan as a main chain and β-1,6-glucan as a side chain, derived from culture medium of *Schizophyllum commune* (GANN, 60, 137–144 (1969)).

The mechanisms of action of such immunoactivating agent are considered such that it acts on lymphocytes to cause secretion of an endogenous TNF (tumor necrosis factor) or a TNF-like substance and thereby increase the in vivo TNF activity and, as a result, an antitumor effect is produced.

Although such immunoactivating agents do not produce severe adverse effects and are useful antitumor agents, their activity is not so potent and satisfactory effects are not always obtained.

SUMMARY OF THE INVENTION

As a result of their intensive investigations made in an attempt to increase the activity of immunoactivating agents, the present inventors found for the first time that the combined use of an immunoactivating agent and a CSF can increase the in vivo TNF activity.

They further found that CSFs remarkably increase the antitumor effect of immunoactivating agents and that, therefore, said CSFs are usable as adjuvants in cancer immunotherapy with immunoactivating agents, in other words as potentiators for immunoactivating agents. The present invention has been completed on the basis of these findings.

DETAILED DESCRIPTION OF THE INVENTION

(1) CSF

The CSF to be used in accordance with the invention is not limited to any particular species but may be any proteinous factor capable of promoting the proliferation and differentiation of granulocytes and macrophages.

As examples of such CSF, there may be mentioned the known G-CSF, M-CSF (including CSF-HU) and GM-CSF, among others. M-CSF is preferably used in the present invention.

The CSFs can be prepared, for example, by such means as purification from human urine, cultivation of CSF-producing cells or genetic engineering techniques.

More specifically, there may be mentioned, among others:

The CSF disclosed in U.S. Pat. No. 4,275,056 (hereinafter referred to as "CSF (i)");

The CSF disclosed in JP-A-63-54398 (hereinafter referred to as "CSF (ii)") (the term "JP-A" used herein means "an unexamined published Japanese patent application");

The CSF disclosed in JP-A-63-290900 (hereinafter referred to as "CSF (iii)"); and The CSF dislocsed in JP-A-63-250400 (hereinafter referred to as "CSF (iv)").

(i) CSF (i)

The CSF (i) is a glycoprotein having the following physicochemical properties:

(a) Molecular weight: 75,000–90,000 as measured by the gel filtration method;

(b) Solubility: It is soluble in water, slightly soluble in chloroform, and insoluble in ethyl alcohol and acetone;

(c) Specific rotation: $[\alpha]_D^{20} = 0 \pm 40$ (0.25% aqueous solution);

(d) pH: 5.0–6.0 for 1% (by weight) aqueous solution;

(e) Isoelectric point: pH 4.7±0.2;

(f) Temperature stability: A 1% (by weight) aqueous solution, when heated at 60° C. ±0.5° C. for 30 minutes, loses its ability to promote the differentiation and proliferation of human granulocytes;

(g) Electrophoresis: Its molecular weight determined by electrophoresis on a sodium dodecyl sulfate-polyacrylamide gel is 85,000;

(h) Infrared absorption: It has the following characteristic absorptions (cm$^{-}$):
3600–3200 (strong), 1700–1600 (strong), 1550 (medium), 1430–1380 (medium), 1150–1000 (broad);

(i) Color reactions: Positive sugar color reactions in α-naphthol-sulfuric acid reaction, indole-sulfuric acid reaction, anthrone-sulfuric acid reaction and phenol-sulfuric acid reaction; positive peptide bond and amino acid color reactions in Lowry-Folin reaction and in ninhydrin reaction after hydrolysis with hydrochloric acid;

(j) Constituent amino acids in the protein moiety: Proline, aspartic acid, threonine, serine, glutamic acid, glycine, alanine, valine, methionine, isoleucine, leucine, thyrosine, phenylalanine, lysine, histidine, tryptophan and arginine;

(k) Color and appearance: Almost white, and amorphous;

(l) Constituent carbohydrates in the sugar moiety: Neutral carbohydrates (as glucose) 10.0–13.0% (by weight), sialic acids 3.0–7.0% (by weight), amino sugars not more than 1% (by weight);

(m) Proportions of protein and carbohydrate: Protein 75–85% (by weight), sugar 13.0–20.0% (by weight);

| (n) Elemental analysis: | |
| --- | --- |
| Carbon: | 42.3–47.3% |
| Hydrogen: | 5.7–7.8% |
| Nitrogen: | 9.6–14.3%, |
| Sulfur: | not more than 0.2%; |

(o) It acts on human marrow cells and promotes the differentiation and proliferation of granulocytes., Some methods of producing said glycoprotein are disclosed in U.S. Pat. Nos. 4,275,056 and 4,230,697, and GB-A-2 016 477. One preparation example is set forth below.

More specifically, there may be mentioned, for example, a method for obtaining CSF (i) which comprises bringing human urine into contact with a silicon-containing adsorbent, eluting the active substance adsorbed with an aqueous alkali solution, concentrating with a neutral salt, collecting the resulting precipitate fraction, removing substances having a molecular weight less than $10^4$ from said fraction, dissolving the thus-obtained fraction containing substances having a molecular weight of $10^4$ or more in an inorganic salt buffer solution, bringing the solution into contact with a cation exchanger to thereby remove impurities by adsorption on said ion exchanger, bringing the effluent or eluate solution into contact with an anion exchanger, eluting the active substance adsorbed on said ion exchanger with an inorganic salt solution having a concentration of 0.1–0.3 mole per liter, applying the eluate obtained to a column packed with a highly crosslinked polymeric gel having a water absorbency of 10–20 ml/g, developing the active substance in said eluate with a salt buffer solution having a concentration of 0.05–0.1 mole per liter, collecting fractions of a relative elution volume of 1.11–1.60, bringing the thus-collected fractions into contact with a glycophilic adsorbent at pH 6.0–8.0, eluting the active substance with a 1.0–2.0 M salt-added buffer solution (pH 6.0–8.0) containing 20–100 mM sugar, subjecting the eluate to preparative electrophoresis at pH 7.0–9.0, eluting the active substance with a dilute salt solution, and recovering the active ingredient.

The active substance may be heat-treated at 50°–70° C. and at pH 5–9 for about 8–30 hours, if necessary.

(ii) CSF (ii)

The CSF (ii) is a glycoprotein having the following properties:
(a) Molecular weight: About 70,000 as measured by the gel filtration method;
(b) Isoelectric point: pH about 4.7;
(c) N-Terminal amino acid sequence:

| 1 | 2 | 3 | 4 | 5 | 6 | 7 |
| --- | --- | --- | --- | --- | --- | --- |
| Ser | Pro | Ser | Gly | — | Gln | — |

| 8 | 9 | 10 | 11 | 12 | 13 | 14 |
| --- | --- | --- | --- | --- | --- | --- |
| Ser | Gln | Pro | Gln | Thr | Val | Phe |

| 15 | 16 | 17 | 18 | 19 | 20 |
| --- | --- | --- | --- | --- | --- |
| — | Thr | Ala | — | Gln | Gly |

(In the above sequence, "—" means that the amino acid residue in question cannot be identified.)

(d) It acts on marrow cells and promotes the differentiation and proliferation of granulocytic series stem cells;
(e) Proportions of protein and carbohydrate: Carbohydrate content about 13–20%.

A method of producing the CSF (ii) is disclosed in JP-A-63-54398, for instance. More specifically, the following method may be mentioned as an example.

A. STARTING MATERIAL

A solution having human CSF activity as derived from human urine or the like, in particular from human urine, by partial purification to a specific CSF activity of at least about 1,000–3,000 units/A280 (absorbance at 280 nm) can be used. The partial purification can be carried out by a known method, for example the method described in U.S. Pat. No. 4,275,506 (purification by treatment with a silicon-containing adsorbent, a cation exchanger and an anion exchanger, and gel filtration) or in JP-A-59-58629 (purification by concentration, heating, and treatment with polyethylene glycol (PEG) and an anion exchanger).

B. PURIFICATION AND ISOLATION

The purification and isolation may be performed by subjecting the partially purified CSF to a combination of PEG fractionation, ethanol fractionation, ion exchange chromatography, gel filtration, hydrophobic chromatography and HPLC (high-performance liquid chromatography).

(iii) CSF (iii)

The CSF (iii) is a monomeric glycoprotein and has the following properties:
(a) Molecular weight: About 70,000 as determined by the gel filtration method; about 34,000 as determined by SDS-PAGE (sodium dodecyl sulfate-polyacrylamide gel electrophoresis) under nonreducing as well as reducing conditions;

(b) N-Terminal amino acid sequence:

```
1                    5                       10
Glu—Glu—Val—Ser—Glu—Tyr—X—Ser—His—Met—

15                      20
Ile—Gly—Ser—Gly—His—Leu—Gln—Ser—Ler—Gln—

X—Leu—Ile—Asp—
```

(In the above sequence, "X" means that the amino acid residue in question has not been identified as yet.)

(c) It acts on marrow cells and promotes the differentiation and proliferation of granulocytic series stem cells.

A method of producing the CSF (iii) is disclosed in JP-A-63-290900, for instance.

(iv) CSF (iv)

The CSF (iv) is, described in JP-A-63-250400, a glycoprotein having the following physicochemical properties:

(a) MOLECULAR WEIGHT

It is a homodimer composed of two identical subunits and, when determined by sodium dodecyl sulfate-polyacrylamide gel electrophoresis (SDS-PAGE), its molecular weight is 70,000–90,000 daltons. The molecular weight of the subunit resulting from dissociation with a reducing agent and not retaining biological activity as determined by SDS-PAGE is 35,000–45,000 daltons.

(b) AMINO ACID SEQUENCE OF SUBUNIT

The subunit protein constituting the homodimer has the amino acid sequence shown below, which contains 214–238 amino acid residues. The 122nd and 140th amino acid (asparagine) residues each has a typical N-glycoside binding site representable by asparagine (Asn)-X-threonine (Thr)/serine (Ser), where X is an optionally selected amino acid residue.

SUBUNIT AMINO ACID SEQUENCE

```
1
Glu—Glu—Val—Ser—Glu—Tyr—Cys—Ser—His—Met
—Ile—Gly—Ser—Gly—His—Leu—Gln—Ser—Leu—Gln
—Arg—Leu—Ile—Asp—Ser—Gln—Met—Glu—Thr—Ser
—Cys—Gln—Ile—Thr—Phe—Glu—Phe—Val—Asp—Gln
                                          50
—Glu—Gln—Leu—Lys—Asp—Pro—Val—Cys—Tyr—Leu
—Lys—Lys—Ala—Phe—Leu—Leu—Val—Gln—Asp—Ile
—Met—Glu—Asp—Thr—Met—Arg—Phe—Arg—Asp—Asn
—Thr—Pro—Asn—Ala—Ile—Ala—Ile—Val—Gln—Leu
—Gln—Glu—Leu—Ser—Leu—Arg—Leu—Lys—Ser—Cys
                                         100
—Phe—Thr—Lys—Asp—Tyr—Glu—Glu—His—Asp—Lys
—Ala—Cys—Val—Arg—Thr—Phe—Tyr—Glu—Thr—Pro
—Leu—Gln—Leu—Leu—Glu—Lys—Val—Lys—Asn—Val
—Phe—Asn—Glu—Thr—Lys—Asn—Leu—Leu—Asp—Lys
—Asp—Trp—Asn—Ile—Phe—Ser—Lys—Asn—Cys—Asn
                                         150
—Asn—Ser—Phe—Ala—Glu—Cys—Ser—Ser—Gln—Asp
—Val—Val—Thr—Lys—Pro—Asp—Cys—Asp—Cys—Leu
—Tyr—Pro—Lys—Ala—Ile—Pro—Ser—Ser—Asp—Pro
—Ala—Ser—Val—Ser—Pro—His—Gln—Pro—Leu—Ala
—Pro—Ser—Met—Ala—Pro—Val—Ala—Gly—Leu—Thr
                                         200
—Trp—Glu—Asp—Ser—Glu—Gly—Thr—Glu—Gly—Ser
—Ser—Leu—Leu—Pro—Gly—Glu—Gln—Pro—Leu—His
             214
—Thr—Val—Asp—Pro—Gly—Ser—Ala—Lys—Gln—Arg
—Pro—Pro—Arg—Ser—Thr—Cys—Gln—Ser—Phe—Glu
—Pro—Pro—Glu—Thr—Pro—Val—Val—Lys
```

(c) ISOELECTRIC POINT

The isoelectric point (pI) as determined by the polyacrylamide gel isoelectric focusing and sucrose density gradient isoelectric focusing techniques is 3.1–3.7.

(d) SUGAR CHAIN-CONSTITUTING MONOSACCHARIDES

The following sugar chain-constituting monosaccharides have been identified by high-performance liquid chromatography following hydrolysis: mannose, galactose, N-acetylglucosamine, N-acetylgalactosamine and N-acetylneuraminic acid.

(e) CIRCULAR DICHROISM SPECTRUM

The far ultraviolet CD spectrum recorded with a circular dichroism dispersion meter has minimum peaks at the wavelengths 208 and 222 nm, indicating that an α-helix structure is contained.

(f) THERMAL STABILITY

The biological activity is not lost even open heating at 60±0.5° C. for 60 minutes.

(g) INFRARED ABSORPTION

The infrared absorption spectrum shows the following characteristic absorptions ($cm^{-1}$):
3250, 2900, 1640, 1520, 1410, 1180, 1120, 1040.

(h) PHYSIOLOGICAL ACTIVITY

It has colony stimulating activity against mammalian monocyte-macrophage series cells.

A typical method of producing the CSF (iv) comprises adjusting human urine to pH 8–9 to thereby cause precipitation of insoluble matter, desalting the supernatant with an ultrafiltration membrane, concentrating the same at least 200 times, adjusting the concentrate to pH 6.5–7.5, heating the same at 60° C. for 10 hours, removing the resulting precipitate by centrifugation, allowing the active substance to be adsorbed on an anion exchanger, eluting the same with 0.2–0.4M buffer, subjecting the eluate to gel filtration in 1–4M buffer, recovering fractions with a molecular weight of 70,000 or more, allowing said fractions to be adsorbed on a hydrophobic affinitive material, eluting the active substance with 0.5–1M buffer, subjecting the eluate to high-speed liquid gel filtration, recovering fractions with a molecular weight of 70,000–150,000 daltons, adjusting said fractions to pH 1–2, subjecting the same to reversed-phase high-performance liquid chromatography, and eluting the active ingredient. The thus-obtained CSF has a purity such that it has a specific activity of about 100,000–20,000,000 units/mg protein.

The CSFs produced by the methods mentioned above are aseptically lyophilized in vials and sealed therein in the powder form. It is also recommended that an aqueous solution containing human serum albumin (as CSF stabilizer) and an amino acid or a sugar (as dissolution aid) be added to the CSFs to give final concentrations of 1 to 10 w/v%, 0.1 to 5 w/v% and 1 to 10 w/v%, respectively, prior to lyophilization and the mixtures be subjected to sterile filtration and then to lyophilization under aseptic conditions.

In biological activity measurement, the colony formation of mouse marrow cells in vitro was used as an activity measurement parameter. Thus, 0.1 ml of a sample supplemented with 20% fetal calf serum and adjusted to a glycoprotein concentration of 10%, McCoy's 5A medium containing 0.3% agar and $7.5 \times 10^4$ mouse marrow cells were added to a plastic culture dish having a diameter of 35 mm, the total volume was adjusted to 1 ml with McCoy's 5A medium containing 0.3% agar, and the dish contents were incubated at 37° C. for 7 days in wet air containing 5% $CO_2$. Thereafter, cell aggregates consisting of 50 or more cells were counted as colonies under an invert microscope.

One colony formed is taken as one unit.

In the practice of the invention, those peptide fragments of said glycoproteins or derivatives of such fragments which have granulocyte differentiation and proliferation promoting activity can also be used as active ingredients. The means of fragmentation, for instance, may be sugar elimination by treatment with a known enzyme, or degradative fragmentation treatment. Genetically engineered peptide fragments having granulocyte differentiation and proliferation promoting activity may also be used.

(2) Immunoactivating agent

The immunoactivating agent to be used in the practice of the invention is not limited to any particular species provided that it functions as an immunoactivating agent to increase TNF activity through its effect on monocytes, granulocytes and lymphocytes, and thus produce an antitumor effect.

Specific examples are Picibanil (OK-432), Krestin (PSK), lentinan and schizophyllan (SPG), among others.

(3) DOSE AND DOSAGE

The CSFs are administered, for example in the form of solutions in physiological saline for injection, distilled water for injection or the like which have a CSF concentration of $10^3$ to $10^6$ units/ml, by intravenous, intramuscular or subcutaneous injection or intravenous drip, etc.

The dose is generally 1,000–150,000 units/kg body weight once or in several times per day but may suitably be increased or decreased depending on the symptom.

The immunoactivating agent can be administered in accordance with the dosage recommended by the manufacturers. Picibanil can be administered intramuscularly, subcutaneously, intravenously, etc. in a dose ranging from 1 to 10 KE in a few times per week. Krestin can be orally administered in a dose of 3 g per day in a few devided doses. The recommended dosage of lentinan is 2 mg per week by intravenous injection or intravenous drip.

The CSFs and the immunoactivating agent may be administered simultaneously or separately.

The concomitant use of CSF and immunoactivating agent has been confirmed to increase the in vivo TNF activity as compared with the use of immunoactivating agent alone and therefore, the CSF can be empolyed to highten the TNF antitumor effect.

Therefore, it is believed that the present invention is very useful in cancer immunotherapy.

The following test examples and working examples illustrate the invention in further detail but are by no means limitative of the scope of the invention.

TEST EXAMPLE 1 (Toxicity)

The glycoprotein prepared in Example 1 below was evaluated for acute toxicity in male C57BL mice by the method of Richard et al. (Journal of Pharmacology and Experimental Therapeutics, vol. 90, page 99, 1949).

The results obtained are shown in Table 1.

TABLE 1

|  | $LD_{50}$ |
|---|---|
| Intraperitoneal administration | $1 \times 10^8$ units/kg |
| Intravenous administration | $1 \times 10^7$ units/kg |
| Subcutaneous administration | $1 \times 10^8$ units/kg |

TEST EXAMPLE 2

Induction of TNF activity by mixed culture of monocytes and PICIBANIL (OK-432) plus CSF (1) Monocytes were separated from heparinized peripheral blood by Ficoll-Hypaque gradient centrifugation and a monocyte suspension ($3.25 \times 10^6$ cells/10 ml) was prepared using 10% human albumin-supplemented RPMI.

(2) To the monocyte suspension were simultaneously added 0.01 KE/ml of Picibanil and human urine-derived CSF obtained in Example 4 (to a specified concentration as shown in Table 2).

(3) Incubation was performed at 37° C. for 72 hours in a 5% $CO_2$ atmosphere.

(4) The supernatant was assayed for TNF activity at timed intervals. The TNF activity was determined by measuring the cytocidal activity against L929 cells in terms of the absorbance of crystal violet. The results thus obtained are shown in Table 2.

TABLE 2

| Additives | | TNF activity (TNF units/ml) | | |
|---|---|---|---|---|
| CSF (units/ml) | PICIBANIL (KE/ml) | After 24 hours | After 48 hours | After 72 hours |
| 0 | 0 | ND | ND | ND |
| $10^3$ | 0 | ND | ND | ND |
| 0 | 0.01 | 1190 | 905 | 297 |
| $10^2$ | 0.01 | 1900 | 1670 | 1580 |
| $10^3$ | 0.01 | 2350 | 1550 | 1060 |
| $10^4$ | 0.01 | 2260 | 1510 | 409 |

Note:
1 KE corresponds to 2.8 mg of Picibanil dry powder.

From the data shown in Table 2, it was found:

(1) That the CSF itself does not cause TNF activity expression (ND = not detected);
(2) That the TNF activity is increased by the combined use of PICIBANIL and the CSF; and
(3) That when both Picibanil and CSF are used in combination, the TNF activity is maintained for a long period.

Meanwhile, it has been confirmed that OSFs do not influence the monocytes count.

EXAMPLE 1

Fresh urine (400 liters) collected from healthy humans was adjusted to pH 8 with 10% sodium hydroxide and then the insoluble matter was removed by centrifugation on a continuous centrifuge at 15,000 r.p.m. with cooling at 0° C.

The thus-obtained supernatant was adjusted to pH 7 with 10% hydrochloric acid and applied to a column (10 $\times$ 80 cm) packed with silica gel. The fraction adsorbed on the silica gel was eluted with 40 liters of 5% ammonia water.

The eluate obtained was adjusted to pH 7.5 with 1N sulfuric acid, powdery ammonium sulfate was added thereto to 70% saturation, the resultant mixture was allowed to stand overnight at 0° C. and the resultant precipitate was collected by filtration.

The precipitate was dissolved in 2 liters of 5% ammonia water, the solution was placed in a dialysis tube (Visking) and dialyzed against 0.05M phosphate buffer (pH 6.5) to a satisfactory extent, the same buffer as mentioned just above was added to the dialyzate to make a total volume of 10 liters, and the diluted dialyzate was passed through a CM Sephadex C-50 ion exchange (4.0$\times$40 cm) equilibrated in advance with 0.05M phosphate buffer (pH 6.5), for adsorption of impurities on the ion exchange resin.

The eluate (10 liters) was concentrated in a Diaflo hollow fiber concentrator (Amicon model DO-30), the concentrate was dialyzed against 0.1M Tris-hydrochloride buffer (pH 7.0) overnight at 5° C. in the same manner as mentioned above, and the same buffer was added to the dialyzate to adjust the whole volume to 3 liters.

Thus, the glycoprotein-containing crude aqueous solution was obtained.

This solution was applied to a DEAE-cellulose column (4.0×40 cm) equilibrated and activated in advance with the same buffer. After sufficient washing of the column with 0.1M Tris-hydrochloride buffer (pH 7.0), elution was carried out with 0.1M Tris-hydrochloride buffer (pH 7.0) containing 0.3M sodium chloride. Fractions having granulocyte differentiation and proliferation promoting activity were collected and dialyzed against 0.1M Tris-hydrochloride buffer (pH 7.0).

The dialyzate obtained was again applied to a DEAE-cellulose column (4.0×40 cm) equilibrated and activated in advance with the same buffer. Elution was carried out by the linear concentration gradient elution technique with 0.1 to 0.3M sodium chloride, fractions having granulocyte differentiation and proliferation promoting activity were collected, powdery ammonium sulfate was added to these fractions (combined) to 70% saturation, and the resultant precipitate was collected, dissolved in a small amount of 0.1M Tris-hydrochloride buffer (pH 7.0) and dialyzed against the same buffer to give a dialyzate.

Then, 20 ml of said dialyzate was developed on a Sephadex G-150 column (4.0×60 cm) equilibrated in advance with 0.1M Tris-hydrochloride buffer (pH 7.0), fractions of an elution coefficient (Ve/Vo) of 1.11–1.45 were collected and dialyzed against distilled water, and the dialyzate was lyophilized to give about 500 mg of a powder.

Then, 200 mg of the above powder was dissolved in 0.02M phosphate buffer (pH 7.0) containing 1.0M sodium chloride, the solution was applied to a column containing 100 ml of concanavalin A-Sepharose 4B (Fine Chemical Laboratories) equilibrated in advance with the same buffer, the column was washed sufficiently with 0.02M phosphate buffer (pH 7.0) containing 1.0M sodium chloride, then elution was carried out with 0.02M phosphate buffer (pH 7.0) containing 50 mM $\alpha$-methyl-D-glucoside and 1.0M sodium chloride, fractions having granulocyte differentiation and proliferation promoting activity were collected and dialyzed against distilled water, and the dialyzate was lyophilized.

Further, about 50 mg of the thus-obtained lyophilizate powder was dissolved in 1 ml of 0.125M Tris-hydrochloride buffer (pH 6.8) containing 10% glycerin and electrophoresed on a 8% acrylamide gel (pH 8.9; 25 mm×100 mm) in a preparative electrophoresis apparatus (LKB model Unifork 900) at an electric current of 10 mA while cooling water was passed through the apparatus. A fraction of a relative mobility of 0.46 was recovered with 0.025M Tris-glycine buffer (pH 8.3) and dialyzed against distilled water, and the dialyzate was lyophilized to give about 10 mg of a glycoprotein usable in the practice of the invention.

The above procedure was repeated to give about 1 g of the glycoprotein. To 1 g of the thus-obtained purified glycoprotein was added 10 ml of water for complete dissolution of the glycoprotein, and the pH was adjusted to 6.8 by adding 10% aqueous sodium hydroxide.

The solution was then heated at 60° C. for 10 hours, then cooled rapidly with ice water and diluted 10 times by adding sterilized water, the dilution was filter sterilized with a filtration sterilization apparatus equipped with a membrane filter (pore size 0.45 $\mu$) (Millipore) and the filtrate was aseptically distributed in 1-ml portions into glass vials dry air-sterilized in advance at 180° C. for 2 hours, the vial contents were lyophilized aseptically, and the vials were sealed. Thus were obtained about 97 vials each containing 1 mg of the heat-treated glycoprotein. The purified glycoprotein has a specific activity of $1 \times 10^7$ units/mg protein.

EXAMPLE 2

From 1,000 liters of fresh urine collected from healthy humans, 2.5 liters of a glycoprotein-containing crude aqueous solution was obtained in the same manner as in Example 1. To this aqueous solution was added 25 liters of 0.1M Tris-hydrochloride buffer (pH 7.0), and the mixture was stirred sufficiently and then again concentrated to about 1/25 in a Diaflo hollow fiber high-speed concentrator. Then, 5 liters of 0.1M Tris-hydrochloride buffer (pH 7.0) and 5 liters of a DEAE-cellulose dispersion (containing 200 g of DEAE on the dry basis) equilibrated in advance with 0.1M Tris-hydrochloride buffer (pH 7.0) were added to the concentrate, the mixture was stirred for 30 minutes and then allowed to stand, and said cellulose was collected by suction filtration. To said cellulose collected by filtration was added 10 liters of 0.1M Tris-hydrochloride buffer (pH 7.0) for washing, and said cellulose was collected again by suction filtration, washed with 10 liters of 0.1M Tris-hydrochloride buffer (pH 7.0) containing 0.05M sodium chloride and collected by suction filtration. To the cellulose thus filtered off was added 10 liters of 0.1M Tris-hydrochloride buffer (pH 7.0) containing 0.3M sodium chloride, and a glycoprotein-containing fraction was eluted from said DEAE-cellulose by stirring the mixture. The eluate was desalted by repeated dilution with distilled water and concentration using a Diaflo hollow fiber high-speed concentration apparatus (model DC-30) and then lyophilized to give about 15 g of a powder. The thus obtained lyophilizate powder was dissolved in 150 ml of distilled water, the solution was applied to a Sephadex G-150 column (6.0×80 cm) equilibrated in advance with 0.1M Tris-hydrochloride buffer (pH 7.0), and glycoprotein-containing fractions corresponding to an elution coefficient of 1.11–1.60 were collected. Said fractions were dialyzed sufficiently against distilled water, and the dialyzate was concentrated using a Diaflo hollow fiber concentration apparatus (model DC2) to give 100 ml of a concentrate containing about 9 g of a crude glycoprotein. To this concentrate was added 0.1M citric acid-sodium phosphate buffer, the pH was adjusted to 6.1, the solution was heat-treated in the same manner as in Example 1, filter sterilized, distributed in 2.5-ml portions into vials under aseptic conditions and lyophilized under aseptic conditions, and the vials were sealed. Thus were obtained 40 vials each containing about 3.8 mg of the heat-treated glycoprotein. The purified glycoprotein has a specific activity of $1 \times 10^7$ units/mg protein.

EXAMPLE 3

Urine (200 liters) collected from healthy humans was adjusted to pH 8.5, the resultant precipitate was removed by filtration, and the filtrate was concentrated and desalted with an ultrafiltration membrane (Amicon; H10×50; cut-off molecular weight: 50,000 daltons). The concentrate was then adjusted to pH 7.0 and heated at 60° C. in a hermetically closed vessel for 10 hours for sterilization. Thereafter, the resultant precipitate was removed by centrifugation (5,000×g, 30 minutes), and the supernatant was admixed with DEAE-cellulose equilibrated with 0.02M phosphate buffer (pH 7.2), for adsorption. After washing the DEAE-cellulose with 0.02M phosphate buffer and then 0.02M phosphate buffer (pH 7.2) supplemented with 0.05M sodium chloride, elution was carried out by treating the DEAE-cellulose with 0.25M phosphate buffer supplemented with sodium chloride (pH 7.2). The eluate was concentrated with an ultrafiltration membrane (Amicon; HIP10) and then subjected to gel filtration using Sephacryl S-300 (Pharmacia, $\phi 4 \times 80$ cm) with a buffer (pH 7.2) supplemented with 1M ammonium sulfate. The fractions corresponding to the molecular weight range of 70,000-150,000 daltons as obtained in the above gel filtration were combined and applied to a phenyl-Sepharose 4B column (Pharmacia, $\phi$ 2×20 cm) equilibrated with the above-mentioned buffer supplemented with 1M ammonium sulfate, for adsorption. Elution was carried out with a buffer (pH 7.2) supplemented with 0.5M ammonium sulfate. The eluate was concentrated with an ultrafiltration membrane (Asahi chemical Industry, NM-3), and the concentrate was subjected to high-performance liquid chromatography using TSKG-3,000SW columns (Tosoh Corporation, $\phi 4 \times 600$ mm×2) to give a fraction having the molecular weight range of 70,000-150,000 daltons. This fraction was again concentrated and subjected to high-performance liquid chromatography, which was performed on a reversed-phase Hi-Pore RP-304 (Bio-Rad, $\phi 4 \times 150$ mm) column on a linear acetonitrile concentration gradient (0–100%, pH 2.0). The eluent contained 0.1M trifluoroacetic acid. Thus was eluted a purified CSF, which had a specific activity of $1.4 \times 10^8$ units per milligram of protein.

EXAMPLE 4

CSF was isolated and purified in the same manner as in Example 3 except that high performance liquid chromatography with TSKG-3,000SW (Tosoh Corporation, HLC-837) and phenyl-5pw (Tosoh Corporation) were carried out in place of the treatments with Sephacryl S-300 and phenyl-Sepharose 4B, respectively. The resulting CSF has a specific activity of $1.5 \times 10^8$ units/mg protein.

EXAMPLE 5

(1) Physicochemical Properties of the CSF

The physicochemical properties of the CSF obtained in Example 3 was determined as set forth below.

a) MOLECULAR WEIGHT

The molecular weight determined by sodium dodecyl sulfate-polyacrylamide gel electrophoresis in the absence of any reducing agent by the method of Laemmli (Nature, vol. 227, pages 680-685, 1970) was 70,000-90,000 daltons.

Molecular weight determination performed by the same method but following reduction with 0.2M mercaptoethanol revealed that the CSF had been dissociated into subunits each having a molecular weight of 35,000-45,000 daltons.

b) AMINO ACID SEQUENCE OF SUBUNIT PROTEIN

The purified CSF was analyzed for NH$_2$-terminal amino acid sequence in the conventional manner with a vapor-phase amino acid sequencer. The purified CSF was then denatured with 6M guanidine and alkylated with monoiodoacetic acid and, after desalting, subjected to digestion with trypsin, followed by decomposition with cyanogen bromide. The trypsin-digestion-cyanogen bromide-decomposition product (peptide mixture) was fractionated by reversed-phase high-performance liquid chromatography using Vydac C-18. The peptide fractions separated were each analyzed with a vapor-phase aminoacid sequencer for determining the amino acid sequence of each peptide fragment. Based on the amino acid sequences of the respective trypsin digestion-cyanogen bromide decomposition product peptide fragments and the base sequence of the mRNA cloned by the present inventors, the primary amino acid structure of the subunit protein was determined. The results of sequencing are as shown in Table 3.

The sequence from the NH$_2$-terminal amino acid (glutamic acid) to the 149th amino acid (glutamic acid) is identical to that of CSF-1, which is a known CSF, but the sequence from the 150th to 214th-238th amino acid (65-89 amino acids) is quite different from that of the known CSF.

As the COO-terminal amino acid, proline was detected as the 214th amino acid, and lysine as the 238th amino acid, depending on the molecular weight of the subunit protein. The 122nd and the 140th amino acid (asparagine) each has a typical N-glycoside binding structure of the formula Asn-X-Ser/Thr (X being an optional amino acid) and it is thought that these sites are the sites of sugar chain binding.

TABLE 3

Subunit amino acid sequence

1
Glu—Glu—Val—Ser—Glu—Tyr—Cys—Ser—His—Met—Ile—Gly—Ser—Gly—His—Leu—Gln—Ser—Leu—Gln—

—Arg—Leu—Ile—Asp—Ser—Gln—Met—Glu—Thr—Ser—Cys—Gln—Ile—Thr—Phe—Glu—Phe—Val—Asp—Gln—

50
—Glu—Gln—Leu—Lys—Asp—Pro—Val—Cys—Tyr—Leu—Lys—Lys—Ala—Phe—Leu—Leu—Val—Gln—Asp—Ile—

—Met—Glu—Asp—Thr—Met—Arg—Phe—Arg—Asp—Asn—Thr—Pro—Asn—Ala—Ile—Ala—Ile—Val—Gln—Leu—

100
—Gln—Glu—Leu—Ser—Leu—Arg—Leu—Lys—Ser—Cys—Phe—Thr—Lys—Asp—Tyr—Glu—Glu—His—Asp—Lys—

—Ala—Cys—Val—Arg—Thr—Phe—Tyr—Glu—Thr—Pro—Leu—Gln—Leu—Leu—Glu—Lys—Val—Lys—Asn—Val—

—Phe—Asn—Glu—Thr—Lys—Asn—Leu—Leu—Asp—Lys—Asp—Trp—Asn—Ile—Phe—Ser—Lys—Asn—Cys—Asn—

150
—Asn—Ser—Phe—Ala—Glu—Cys—Ser—Ser—Gln—Asp—Val—Val—Thr—Lys—Pro—Asp—Cys—Asn—Cys—Leu—

TABLE 3-continued

Subunit amino acid sequence

—Tyr—Pro—Lys—Ala—Ile—Pro—Ser—Ser—Asp—Pro—Ala—Ser—Val—Ser—Pro—His—Gln—Pro—Leu—Ala—

200
—Pro—Ser—Met—Ala—Pro—Val—Ala—Gly—Leu—Thr—Trp—Glu—Asp—Ser—Glu—Gly—Thr—Glu—Gly—Ser—

214
—Ser—Leu—Leu—Pro—Gly—Glu—Gln—Pro—Leu—His—Thr—Val—Asp—Pro—Gly—Ser—Ala—Lys—Gln—Arg—

238
—Pro—Pro—Arg—Ser—Thr—Cys—Gln—Ser—Phe—Glu—Pro—Pro—Glu—Thr—Pro—Val—Val—Lys— c) ISOELECTRIC POINT

The isoelectric point (pI) as determined by the polyacrylamide gel isoelectric focusing and sucrose density gradient isoelectric focusing techniques is 3.1–3.7.

d) SUGAR CHAIN-CONSTITUTING MONOSACCHARIDES

The constituent monosaccharides contained in the sugar chains bound to the polypeptide were analyzed by high-performance liquid chromatography following hydrolysis for liberation thereof. Aldoses and sialic acids were fractionated on an anion exchange column and hexosamines on a cation exchange column, elution being carried out by the borate buffer concentration gradient elution technique. The constituents were then subjected to post-column labelling with cyanoacetamide or arginine and identified by the fluorescence method. The sugar chains contained in the CSF molecule are variable, hence were difficult to quantitate, although mannose, galactose, N-acetylglucosamine, N-acetylgalactosamine and N-acetylneuraminic acid were identified as constituent monosaccharides.

e) Circular Dichroism (CD) Spectrum

The CD spectrum in the far ultraviolet region was measured using a circular dichroism dispersion meter (JASCO model J-600). Minimun peaks are observed at the wavelengths 208 nm and 222 nm. It is therefore estimable that the secondary structure of the CSF contains an α-helix structure.

f) THERMAL STABILITY

The CSF was dissolved in a dilute buffer (pH 7.0) to a concentration of 1 μg/ml, and the solution was heated at 60°±0.5° C. for 60 minutes and then assayed for colony stimulating activity (to be mentioned later herein). Almost no activity decrease was observed.

g) INFRARED ABSORPTION SPECTRUM

The infrared absorption spectrum of the CSF in the form of a lyophilized powder was determined by the transmission method (KBr window) using a Fourier-transform infrared spectrophotometer (Nocolet model 5DXC).

The CSF shows strong absorption at 1650 cm$^{-1}$, 1201 cm$^{-1}$ and 1133 cm$^{-1}$, and medium absorption at 1537 cm$^{-1}$, 1432 cm$^{-1}$ and 1068 cm$^{-1}$.

(2) Biological Properties of the CSF

The colony stimulating activity of the CSF obtained in Example 3 was determined by the method involving colony formation of mouse marrow cells on a single-layer soft agar gel. Thus, the CSF sample was admixed with 1 ml of McCoy's 5A medium containing 0.3% agar, 20% fetal calf serum (FCS) and $1 \times 10^5$ mouse marrow cells. Incubation was carried out at 37° C. for 7 days under a stream of 7.5% $CO_2$-containing air. Thereafter, cell aggregates consisting of 50 or more cells were judged as colonies and counted. The colony stimulating activity was expressed in units. One unit was defined as the quantity of CSF required for the formation of one colony. The specific activity was expressed in terms of the number of colonies (units) formed per milligram of the CSF protein. As a result, the CSF according to the invention was found to have a specific activity of $1.4 \times 10^8$ units per milligram of protein. The colonies formed were stained with hematoxylin-eosin for morphological classification. It was thus found that at least 95% of the colonies formed were monocyte-macrophage colonies.

While the invention has been described in detail and with reference to specific embodiments thereof, it will be apparent to one skilled in the art that various changes and modifications can be made therein without departing from the spirit and scope thereof.

What is claimed is:

1. In a process in which an in vivo tumor necrosis factor activity is produced in a patient by administration of a cancer immunoactivating agent to the patient, the improvement which comprises administering to said patient a colony stimulating factor in an amount sufficient to enhance said in vivo tumor necrosis factor activity, said colony stimulating factor having the following properties:

(a) molecular weight
      it is a homodimer composed of two identical subunits and, when determined by sodium dodecyl sulfate-polyacrylamide gel electrophoresis (SDS-PAGE), its molecular weight is 70,000–90,000 daltons: the molecular weight of the subunit resulting from dissociation with a reducing agent and not retaining biological activity as determined by SDS-PAGE is 35,000–45,000 daltons.

(b) amino acid sequence of subunit:
      the subunit protein constituting the homodimer has the amino acid sequence shown below, which contains 214–238 amino acid residues: the 122nd and 140th amino acid (asparagine) residues each has a typical N-glycoside binding site representable by asparagine (Asn)-X-threonine (Thr)/serine (Ser), where X is an optionally selected amino acid residue:

subunit amino acid sequence

1
Glu—Glu—Val—Ser—Glu—Tyr—Cys—Ser—His—Met
—Ile—Gly—Ser—Gly—His—Leu—Gln—Ser—Leu—Gln

―Arg―Leu―Ile―Asp―Ser―Gln―Met―Glu―Thr―Ser
―Cys―Gln―Ile―Thr―Phe―Glu―Phe―Val―Asp―Gln
                                                        50
―Glu―Gln―Leu―Lys―Asp―Pro―Val―Cys―Tyr―Leu
―Lys―Lys―Ala―Phe―Leu―Leu―Val―Gln―Asp―Ile
―Met―Glu―Asp―Thr―Met―Arg―Phe―Arg―Asp―Asn
―Thr―Pro―Asn―Ala―Ile―Ala―Ile―Val―Gln―Leu
―Gln―Glu―Leu―Ser―Leu―Arg―Leu―Lys―Ser―Cys
                                                        100
―Phe―Thr―Lys―Asp―Tyr―Glu―Glu―His―Asp―Lys
―Ala―Cys―Val―Arg―Thr―Phe―Tyr―Glu―Thr―Pro
―Leu―Gln―Leu―Leu―Glu―Lys―Val―Lys―Asn―Val
―Phe―Asn―Glu―Thr―Lys―Asn―Leu―Leu―Asp―Lys
―Asp―Trp―Asn―Ile―Phe―Ser―Lys―Asn―Cys―Asn
                                                        150
―Asn―Ser―Phe―Ala―Glu―Cys―Ser―Ser―Gln―Asp
―Val―Val―Thr―Lys―Pro―Asp―Cys―Asp―Cys―Leu
―Tyr―Pro―Lys―Ala―Ile―Pro―Ser―Ser―Asp―Pro
―Ala―Ser―Val―Ser―Pro―His―Gln―Pro―Leu―Ala
―Pro―Ser―Met―Ala―Pro―Val―Ala―Gly―Leu―Thr
                                                        200
―Trp―Glu―Asp―Ser―Glu―Gly―Thr―Glu―Gly―Ser
―Ser―Leu―Leu―Pro―Gly―Glu―Gln―Pro―Leu―His
                                    214
―Thr―Val―Asp―Pro―Gly―Ser―Ala―Lys―Gln―Arg
―Pro―Pro―Arg―Ser―Thr―Cys―Gln―Ser―Phe―Glu
―Pro―Pro―Glu―Thr―Pro―Val―Val―Lys (c) isoelectric point:
  the isoelectric point (pI) as determined by the polyacrylamide gel isoelectric focusing and sucrose density gradient isoelectric focusing techniques is 3.1–3.7:
(d) sugar chain-constituting monosaccharides:
  the following sugar chain-constituting monosaccharides have been identified by high-performance liquid chromatography following hydrolysis: mannose, galactose, N-acetylglucosamine, N-acetylgalactosamine and N-acetyl-neuraminic acid:
(e) circular dichroism spectrum:
  the far ultraviolet CD spectrum recorded with a circular dichroism dispersion meter has minimum peaks at the wavelengths 208 and 222 nm, indicating that an α-helix structure is contained.
(f) thermal stability:
  the biological activity is not lost even upon heating at $\alpha° + 0.5°$ C. for 60 minutes:
(g) infrared absorption:
  the infrared absorption spectrum shows the following characteristic absorptions (cm$^{-1}$):
  3250, 2900, 1640, 1520, 1410, 1180, 1120, 1040.
(h) physiological activity:
  it has colony stimulating activity against mammalian monocyte-macrophage series cells.

2. The process of claim 1, wherein said immunoactivating agent is selected form the group consisting of Picibanil, Krestin, lentinan and schizophyllan.

3. The process of claim 1, wherein said colony stimulating factor acts on stem cells of the bone marrow granulocytic and macrophage series cells.

4. The process of claim 1, wherein the colony stimulating factor is a proteinous factor capable of promoting the proliferation and differentiation of granulocytes and macrophages.

5. The process of claim 1, wherein the colony stimulating factor is administered in a dose of 1,000–150,000 units/kg body weight.

6. In a process in which living cells are induced to secret endogenous tumor necrosis factor by a cancer immunoactivating agent, the improvement which comprises providing in the presence of said cells a colony stimulating factor in an amount sufficient to increase the quantity of said tumor necrosis factor secreted by said cells, said colony stimulating factor having the following properties:

(a) molecular weight:
  it is a homodimer composed of two identical subunits and, when determined by sodium dodecyl sulfate-polyacrylamide gel electrophoresis (SDS-PAGE), its molecular weight is 70,000–90,000 daltons: the molecular weight of the subunit resulting from dissociation with a reducing agent and not retaining biological activity as determined by SDS-PAGE is 35,000–45,000 daltons.

(b) amino acid sequence of subunit:
  the subunit protein constituting the homodimer has the amino acid sequence shown below, which contains 214–238 amino acid residues: the 122nd and 140Th amino acid (asparagine) residues each has a typical N-glycoside binding site representable by asparagine (Asn)-X-threonine (Thr)/serine (Ser), where X is an optionally selected amino acid residue:

1
Glu―Glu―Val―Ser―Glu―Tyr―Cys―Ser―His―Met
―Ile―Gly―Ser―Gly―His―Leu―Gln―Ser―Leu―Gln
―Arg―Leu―Ile―Asp―Ser―Gln―Met―Glu―Thr―Ser
―Cys―Gln―Ile―Thr―Phe―Glu―Phe―Val―Asp―Gln
                                                        50
―Glu―Gln―Leu―Lys―Asp―Pro―Val―Cys―Tyr―Leu
―Lys―Lys―Ala―Phe―Leu―Leu―Val―Gln―Asp―Ile
―Met―Glu―Asp―Thr―Met―Arg―Phe―Arg―Asp―Asn
―Thr―Pro―Asn―Ala―Ile―Ala―Ile―Val―Gln―Leu
―Gln―Glu―Leu―Ser―Leu―Arg―Leu―Lys―Ser―Cys
                                                        100
―Phe―Thr―Lys―Asp―Tyr―Glu―Glu―His―Asp―Lys
―Ala―Cys―Val―Arg―Thr―Phe―Tyr―Glu―Thr―Pro
―Leu―Gln―Leu―Leu―Glu―Lys―Val―Lys―Asn―Val
―Phe―Asn―Glu―Thr―Lys―Asn―Leu―Leu―Asp―Lys
―Asp―Trp―Asn―Ile―Phe―Ser―Lys―Asn―Cys―Asn
                                                        150
―Asn―Ser―Phe―Ala―Glu―Cys―Ser―Ser―Gln―Asp
―Val―Val―Thr―Lys―Pro―Asp―Cys―Asp―Cys―Leu
―Tyr―Pro―Lys―Ala―Ile―Pro―Ser―Ser―Asp―Pro
―Ala―Ser―Val―Ser―Pro―His―Gln―Pro―Leu―Ala
―Pro―Ser―Met―Ala―Pro―Val―Ala―Gly―Leu―Thr
                                                        200
―Trp―Glu―Asp―Ser―Glu―Gly―Thr―Glu―Gly―Ser
―Ser―Leu―Leu―Pro―Gly―Glu―Gln―Pro―Leu―His
                                    214
―Thr―Val―Asp―Pro―Gly―Ser―Ala―Lys―Gln―Arg
―Pro―Pro―Arg―Ser―Thr―Cys―Gln―Ser―Phe―Glu
―Pro―Pro―Glu―Thr―Pro―Val―Val―Lys (c) isoelectric point:
  the isoelectric point (pI) as determined by the polyacrylamide gel isoelectric focusing and sucrose density gradient isoelectric focusing techniques is 3.1–3.7:
(d) sugar chain-constituting monosaccharides:
  the following sugar chain-constituting monosaccharides have been identified by high-performance liquid chromatography following hydrolysis: mannose, galactose, N-acetylglucosamine, N-acetylgalactosamine and N-acetyl-neuraminic acid:
(e) circular dichroism spectrum:
  the far ultraviolet CD spectrum recorded with a circular dichroism dispersion meter has minimum peaks at the wavelengths 208 and 222 nm, indicating that an α-helix structure is contained:
(f) thermal stability:

the biological activity is not lost even upon heating at 60°+0.5° C. for 60 minutes:

(g) infrared absorption:

the infrared absorption spectrum shows the following characteristic absorptions (cm$^{-1}$):

3250, 2900, 1640, 1520, 1410, 1180, 1120, 1040.

(h) physiological activity:

it has colony stimulating activity against mammalian monocyte-macrophage series cells.

* * * * *